(12) United States Patent
Okamoto et al.

(10) Patent No.: US 9,040,070 B2
(45) Date of Patent: May 26, 2015

(54) MATERIAL FOR INDUCTION OF HARD TISSUE REGENERATION

(75) Inventors: Shinichi Okamoto, Kyoto (JP); Yasuhiko Tabata, Kyoto (JP)

(73) Assignee: Nitto Denko Corporation, Ibaraki (JP)

( * ) Notice: Subject to any disclaimer, the term of this patent is extended or adjusted under 35 U.S.C. 154(b) by 236 days.

(21) Appl. No.: 13/502,627

(22) PCT Filed: Oct. 19, 2010

(86) PCT No.: PCT/JP2010/006203
§ 371 (c)(1),
(2), (4) Date: May 30, 2012

(87) PCT Pub. No.: WO2011/048803
PCT Pub. Date: Apr. 28, 2011

(65) Prior Publication Data
US 2012/0237586 A1    Sep. 20, 2012

(30) Foreign Application Priority Data
Oct. 20, 2009 (JP) .................. 2009-241041

(51) Int. Cl.
| | | |
|---|---|---|
| A61F 2/28 | (2006.01) |
| A61F 2/00 | (2006.01) |
| A61L 27/36 | (2006.01) |
| A61L 27/46 | (2006.01) |
| A61L 27/56 | (2006.01) |

(52) U.S. Cl.
CPC ......... *A61L 27/3645* (2013.01); *A61L 27/3616* (2013.01); *A61L 27/46* (2013.01); *A61L 27/56* (2013.01); *A61L 2430/02* (2013.01)

(58) Field of Classification Search
CPC .. A61L 27/3616; A61L 27/3645; A61L 27/46
USPC ............................................ 424/93.72, 423
See application file for complete search history.

(56) References Cited

U.S. PATENT DOCUMENTS

2005/0042210 A1 *   2/2005   Akai .................. 424/93.72

FOREIGN PATENT DOCUMENTS

| CN | 1319437 A | 10/2001 |
|---|---|---|
| DE | 20 2006 013 761 U1 | 11/2006 |
| JP | 2004-123576 A | 4/2004 |
| JP | 2005-110710 A | 4/2005 |
| JP | 2005-211477 A | 8/2005 |
| WO | 02/40071 A1 | 5/2002 |

OTHER PUBLICATIONS

Zhang et al., *Shanxi Med. J.*, 36(6): 486-488 (2007).
Chinese Patent Office, First Office Action in Chinese Patent Application No. 201080047151.2 (Sep. 4, 2013).
Cheng et al., *Chinese J. Orthop. Trauma*, 10(12): 1166-1170 (2008).
Hokugo et al., *Oral Surg. Oral Med. Oral Pathol. Oral Radiol. Endod.*, 104(1): 44-48 (2007).
Hokugo et al., *Tissue Engineering*, 11(7/8): 1224-1233 (2005).
Hokugo et al., *Drug Delivery System*, 18(3): 256, item I-C-27 (2003).
Matsumoto et al., *The Annual Meeting of the Japanese Society for Biomaterials Yokoshu*, 29th, p. 208 (2007).
McClellan et al., *J. Spinal Disord. Tech.*, 19(7): 483-486 (2006).
Morishita et al., *Artificial Organs*, 30(2): 115-118 (2006).
Patel et al., *Spine*, 31(11): 1201-1206 (2006).
Plachokova et al., *Clin. Oral. Impl. Res.*, 17: 305-311 (2006).
Takahashi et al., *Biomaterials*, 26: 3587-3596 (2005).
Takahashi et al., *Biomaterials*, 26: 4856-4865 (2005).
Yamamoto et al., *J. Hard Tissue Biology*, 14(2): 286-287 (2005).
Yurikusa et al., *Hokkaido Journal of Dental Science*, 26(2): 172-181 (2005).
*The Journal of the Japanese Orthopaedic Association*, 84(8): S1039, item 1-3-11 (2010).
Japanese Patent Office, International Search Report in International Patent Application No. PCT/JP2010/006203 (Jan. 18, 2011).
European Patent Office, Extended European Search Report in European Patent Application No. 10824655.4 (Jun. 18, 2014).
Japanese Patent Office, Notice of Reasons for Refusal in Japanese Patent Application No. 2011-537137 (Jun. 10, 2014).
Yaqin et al., *Journal of The Chinese Rare Earth Society*, 25(5): 632-636 (Oct. 2007).
Chinese Patent Office, Third Office Action in Chinese Patent Application No. 201080047151.2 (Jul. 18, 2014).
Chinese Patent Office, Search Report in Chinese Patent Application No. 201080047151.2 (Jul. 9, 2014).

* cited by examiner

*Primary Examiner* — Gina Justice
(74) *Attorney, Agent, or Firm* — Leydig, Voit & Mayer, Ltd.

(57) ABSTRACT

The present invention relates to a material for induction of hard tissue regeneration, comprising platelet-rich plasma and gelatin β-TCP sponge, which promotes angiogenesis, osteogenesis, chondrogenesis and the like.

9 Claims, 5 Drawing Sheets

[comparison]

MATERIAL FOR INDUCTION OF HARD TISSUE REGENERATION

CROSS-REFERENCE TO RELATED APPLICATION(S)

The present application is the U.S. national phase of International Patent Application PCT/JP2010/006203, filed on Oct. 19, 2010, which claims priority to Japanese Patent Application 2009-241041, filed on Oct. 20, 2009.

TECHNICAL FIELD

The present invention relates to a material for induction of hard tissue (e.g., bone or cartilage and the like) regeneration, comprising platelet-rich plasma and gelatin β-TCP sponge.

BACKGROUND ART

Conventionally, autogenous bone transplantation is performed for synostosis of bone fracture part, and reconstruction of bone defective part after excision of benign osteoncus and the like, by harvesting bone from own healthy part and transplanting the bone in the bone defective part. However, due to the invasion on a healthy part, complications are developed in a high rate of about 30%, such as infection of and residual pain in the bone donor site, nerve damage near the bone donor site and the like. In a case where the area of synostosis and bone defect are large, a mass of autogenous bone is necessary, the defective autogenous bone donor site may sometimes cause a clinical problem.

To avoid autogenous bone transplantation and compensate for the shortage of autogenous bone amount, an artificial bone using calcium phosphate and β-tricalcium phosphate (β-TCP) has been used. However, since artificial bone itself does not have an osteoinductive capacity, its applicable site is limited to a comparatively small bone defect under good bone formation environment, and since ossification potential is inferior as compared to autogenous bone, it takes some time to obtain dynamic strength, thus problematically requiring load restriction and rest for a long time after operation. With such background, bone formation techniques with osteoinductive capacity applicable to extensive synostosis and bone defect have been widely studied.

In recent years, a technique for culturing own bone marrow mesenchymal stem cells and transplanting the cells into a bone defective part in combination with an artificial bone has been developed and clinical application has been reported (non-patent document 1). However, it lacks broad utility, since various problems are accumulated in that specialized facilities such as clean room where cell culture can be performed (cell processing center) are necessary, which makes it practically difficult for municipal hospitals to employ the technique, mesenchymal cell with multilineage potential has a risk of canceration, differentiation induction is not necessarily perfect and the like.

Moreover, as a bone formation treatment using a growth factor, bone morphogenetic protein-2 (BMP-2) produced by genetic recombination was approved for use in vertebral body fusion by Food and Drug Administration in Europe and the United States in 1997, and is clinically applied in US. In recent years, however, its effectiveness and safety are questioned. For example, a report has documented that, in lumbar interbody fusion using BMP-2, bone resorption of fixed vertebral body and transplanted bone occurred at high frequency to drastically decrease the synostosis rate. In addition, there are reports on inflammatory reaction in lumbar vertebral peripheral tissues by MRI useful for the evaluation of soft tissues, and severe complications such as difficult breathing due to pharyngeal edema, dysphagia and abnormal swelling of cervical part observed in a case of cervical fixing (non-patent documents 2 and 3). The cause thereof is considered to be edematous change in the soft tissue and vital organs resulting from an antigen-antibody reaction induced by administration of a large amount of artificially-produced growth factor which diffused from the administration site to the peripheral tissues. In addition, since BMP-2 is expensive, it adds several hundreds of thousands of yen to the operation cost, producing a financial burden on patients.

Platelet-rich plasma (also referred to as PRP) is a concentrated platelet plasma obtained by removing red blood cell from peripheral blood by centrifugal separation at a low speed. PRP contains a large amount of growth factors such as platelet-derived growth factor (PDGF) contained in platelet, transforming growth factor β (TGF-β), fibroblast growth factor (FGF), insulin-like growth factor (IGF) and the like, and is known to show effects such as angiogenesis, osteogenesis, promotion of wound healing and the like by a synergistic action of these. It has also been confirmed that a combined use of PRP and an appropriate drug delivery system material such as gelatin hydrogel and the like exhibits osteogenetic activity in long bone and skull bone defect models (patent document 1, non-patent documents 4 and 5).

However, the effect of PRP alone is not sufficient to afford sufficient ossification in large bone defect, anatomically unfused bones, and spinal fusion to joint together spinal bones, and a scaffold having a three-dimensional structure that promotes differentiation and induction of osteoblasts is absolutely necessary.

DOCUMENT LIST

Patent Documents patent document 1: JP-A-2005-211477
patent document 2: JP-A-2004-123576

Non-Patent Documents non-patent document 1: Morishita T, et al., Artif. Organs, 2006
non-patent document 2: Lohn McClellan, et al., J. Spinal Disord. Tech., 2006
non-patent document 3: Ben B, et al., Spine, 2006
non-patent document 4: Hokugo A, et al., Tissue Eng., 2005
non-patent document 5: Hokugo A, et al., Oral Surg. Oral Med. Oral Pathol. Oral Radiol. Endod., 2007

SUMMARY OF THE INVENTION

Problems to be Solved by the Invention

A problem of the present invention is to provide a novel material for the regeneration of a hard tissue such as bone or cartilage and the like, which provides an effect of sustained release of a platelet-rich plasma-derived growth factor, and good scaffolding function for tissue regeneration, and is superior in safety and practicality.

Means of Solving the Problems

To achieve the above-mentioned problem, the inventors have prepared a material for induction of hard tissue regeneration, comprising a gelatin β-TCP sponge obtained by processing gelatin, which is superior as a material for a drug delivery system of growth factor, and β-TCP granules, which are ceramics having bioabsorbability and biodegradability, into a sponge-like form, and platelet-rich plasma (PRP) purified from patient's own blood, which is contained in the sponge. They have verified that the material strikingly enhances ossification in a rat spinal fusion model.

The present invention has been made based on the above-mentioned finding and provides a material for induction of hard tissue regeneration, which contains platelet-rich plasma and gelatin β-TCP sponge.

The hard tissue to which the material of the present invention is applied is a bone or cartilage tissue etc. requiring a scaffold for regeneration, and also includes those in the dental field such as alveolar bone and the like.

The material for induction of hard tissue regeneration of the present invention promotes osteogenesis and chondrogenesis. In addition, the material for induction of hard tissue regeneration of the present invention also promotes angiogenesis.

The material for induction of hard tissue regeneration of the present invention is preferably used for regeneration of hard tissues such as bone or cartilage and the like requiring a scaffold, since the gelatin β-TCP sponge functions as a good cell scaffold for tissue regeneration. However, the application site thereof is not limited to a hard tissue, and it may be a soft tissue in contact with a hard tissue such as bone or cartilage and the like. To be specific, the material induces regeneration of sinew and ligament by its angiogenesis promoting action even in the case of a transplant surgery of a soft tissue such as sinew, ligament etc. in contact with bone or cartilage. Therefore, such use for inducing regeneration of a soft tissue in contact with a hard tissue is also encompassed in the present invention.

The platelet-rich plasma to be used in the present invention is preferably derived from a subject to be applied with a material for induction of hard tissue regeneration. The subject to be applied with the material for induction of hard tissue regeneration of the present invention is not limited to human and includes mammal as a whole.

The gelatin β-TCP sponge to be used in the present invention preferably has a pore size of about 10-500 μm, and gelatin in the gelatin β-TCP sponge is preferably crosslinked. The aforementioned crosslinking is formed by subjecting a composition containing β-TCP and gelatin to crosslinking and freeze-drying. The order of crosslinking and freeze-drying may be any, and a composition after crosslinking may be freeze-dried or a freeze-dried composition may be subjected to crosslinking.

Effect of the Invention

PRP used in the present invention is advantageously free of ethical problems associated with treatments and the risk associated with the use of blood preparations such as virus infection, immuno-incompatibility and the like, since it can be easily harvested from the blood of the subject to be applied with a material for induction of hard tissue regeneration. Moreover, the gelatin β-TCP sponge to be used in the present invention releases a component contained in PRP, such as growth factor and the like, in a sustained manner to promote osteogenesis, chondrogenesis and angiogenesis, as well as functions as a good cell scaffold for tissue regeneration, thereby enabling remarkable bone formation.

Figure 1:
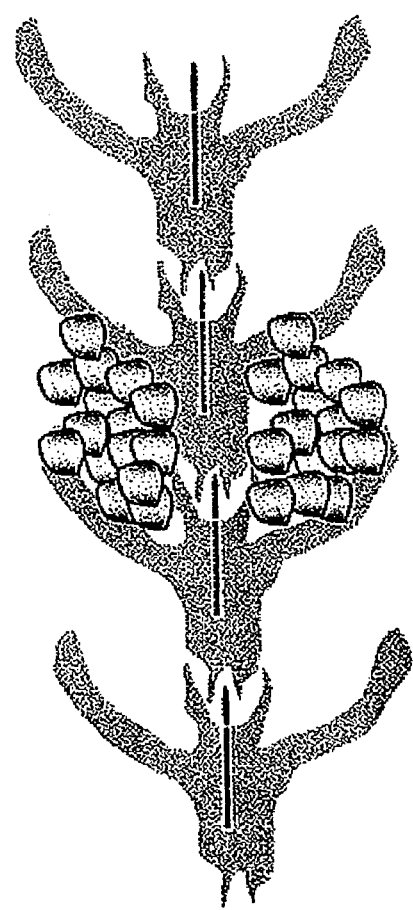
FIG. 1 schematically shows transplantation in between transverse processes 4 and 5 of a rat spinal posterolateral fusion model.

The present specification encompasses the content described in the specification of the priority base application No. 2009-241041.

DESCRIPTION OF EMBODIMENTS

The present invention relates to a material for induction of hard tissue regeneration, which contains platelet-rich plasma (PRP) and gelatin β-TCP sponge.

1. Platelet-Rich Plasma (PRP)

The "platelet-rich plasma (PRP)" of the present invention is a concentrated platelet plasma obtained by removing red blood cell from peripheral blood by centrifugal separation at a low speed. PRP contains a large amount of growth factors such as platelet-derived growth factor (PDGF) contained in platelet, transforming growth factor β (TGF-β), stem cell derived factor (SDF)-1, insulin-like growth factor (IGF) and the like, and is known to show effects such as angiogenesis, osteogenesis, promotion of wound healing and the like by a synergistic action of these.

As for the centrifugation conditions for the preparation of PRP, the rotation number and time for efficient removal of blood cell components can be appropriately determined according to the kind of the centrifugal separator to be used. If necessary, platelets may be concentrated by centrifuging again after removal of the blood cell components. Alternatively, PRP can also be prepared by a blood separator using a membrane.

PRP to be used in the present invention is preferably derived from a subject's own blood, who is in need of administration of the material for induction of hard tissue regeneration of the present invention. However, when the subject has severe anemia or an underlying disease, due to which a blood sample is difficult to obtain, platelet-rich plasma purified from blood of other person may be used.

2. Gelatin β-TCP Sponge

The gelatin β-TCP sponge used in the present invention is a porous sponge-like structure consisting of gelatin and β-TCP granule.

2.1 Gelatin

The gelatin used in the present invention can be obtained by denaturing collagen obtainable from any parts such as skin, bone, sinew and the like of the body of various animal species such as cow, pig, fish and the like, or a substance used as collagen by various treatments such as alkali hydrolysis, acid hydrolysis, enzymatic hydrolysis and the like. While the properties of gelatin vary depending on the material and treatment method to be used, any gelatin having such properties can be utilized as a gelatin β-TCP sponge material in the present invention.

Examples of the measure showing the properties of gelatin include isoelectric point, molecular weight, zeta potential and the like. For example, commercially available gelatin includes type A gelatin manufactured by Sigma Ltd. and gelatin manufactured by Wako Pure Chemical Industries, Ltd., and the zeta potential in an aqueous solution is as follows:

type A gelatin manufactured by Sigma Ltd.: about 0 to about 5 mV gelatin manufactured by Wako Pure Chemical Industries, Ltd.: about −5 to about −2 mV.

The zeta potential is a measure showing the electrostatic charge level of a substance (gelatin).

Particularly preferable gelatin to be used in the present invention has the following properties: acidic gelatin obtained from collagen by an alkali hydrolysis treatment, molecular weight about 10-about 200,000 daltons by SDS-PAGE under non-reduced conditions, and zeta potential in an aqueous solution about −15 to about −20 mV.

Preferably, moreover, acidic gelatin prepared from bovine bone-derived type I collagen by an alkali treatment can be used, which can be obtained from Nitta Gelatin Inc. with an isoelectric point (IEP) 5.0. While a basic gelatin prepared by an acid treatment can also be obtained from Nitta Gelatin Inc. as sample IEP 9.0, the zeta potential is greatly different as shown below.

acidic gelatin (Nitta Gelatin Inc. sample IEP 5.0): about −15 to about −20 mV basic gelatin (Nitta Gelatin Inc. sample IEP 9.0): about +12 to about +15 mV 2.2 β-TCP (β-tricalcium phosphate)

β-TCP (tricalcium phosphate) to be used in the present invention is biodegradable ceramics, which is conventionally used widely as an artificial bone material. The compressive strength of porous β-TCP is about 3M Pa, which is weaker than biological bone (about 7M Pa for cancellous bone) but sufficiently strong for clinical use. β-TCP is gradually decomposed in the body and release calcium ion and phosphoric acid ion to realize an environment that facilitates synthesis of hydroxyapatite, which is a bone constituent component, by osteoblast. That is, β-TCP not only functions as a carrier for a drug delivery system or a scaffold for ossification, but also positively promotes osteogenesis, chondrogenesis, angiogenesis and the like. Thus, β-TCP provides a good scaffold material which increases the dynamic strength of a gelatin sponge obtained by mixing with gelatin, as well as positively promotes osteogenesis, chondrogenesis, angiogenesis and the like. The size, porosity, pore size and the like of β-TCP to be used in the present invention may be any, and any kind of β-TCP granule can be used. For example, commercially available β-TCP-100 (pulverized product): manufactured by Taihei Chemical Industrial Co., Ltd., OSferion (registered trade mark): manufactured by OLYMPUS CORPORATION and the like can be used.

2.3 Structure of Gelatin β-TCP Sponge

The ratio of gelatin and β-TCP in the gelatin β-TCP sponge of the present invention is 10:1-1:10, preferably 5:1-1:5, in dry weight.

The gelatin β-TCP sponge of the present invention is like a sponge having many ultrafine pores having an average pore size of 10-500 μm. Having a structure including many ultrafine pores, the sponge permits easy entry of the surrounding cells thereinto upon transplantation, and can function as a scaffold material for tissue regeneration. Furthermore, sufficient nutrition and oxygen can be supplied to the adhered cells, thus enabling normal cell growth and differentiation.

The lower limit of the average pore size of the ultrafine pores in the gelatin β-TCP sponge of the present invention is 10 μm, and the upper limit thereof is 500 μm. When it is less than 10 μm, since cells cannot enter into a support for tissue engineering, the cell adhesiveness becomes extremely inferior and adhered cells cannot expand three-dimensionally. When it exceeds 500 μm, since the cell density becomes low, tissues and organs cannot regenerate. A preferable lower limit is 50 μm, and a preferable upper limit is 200 μm.

In the gelatin β-TCP sponge of the present invention, gelatin is crosslinked. An index for evaluating the crosslinking level (degree of crosslinking) is water content. The water content is a weight percentage of water in a swollen gelatin β-TCP sponge relative to the weight of the sponge. When the water content is high, the degree of crosslinking of the gelatin β-TCP sponge decreases, and the sponge is easily degraded. That is, the enzymatic degradability of the gelatin β-TCP sponge in the body changes depending on the water content, and the water content affects sustained release (gradual release) of PRP.

The gelatin β-TOP sponge of the present invention preferably has a water content of 90%-99.8%. When the water content is less than 90%, flexibility suitable for transplantation is sometimes impaired, biodegradation may take a long time after transplantation into the body, and a physiologically active substance may remain in a support without being released in a sustained manner. When it exceeds 99.8%, it may occur that a support cannot maintain its strength in a culture medium or buffer, and a physiologically active substance is gradually released only for a short period of 1 to 3 days. More preferable lower limit is 95% and more preferable upper limit is 98%.

2.4 Production Method of Gelatin β-Top Sponge

The gelatin β-TOP sponge to be used in the present invention is obtained by subjecting a composition containing gelatin and β-TOP to crosslinking and freeze-drying.

To be specific, β-TCP is added to gelatin. Then, gelatin is crosslinked. The crosslinking method is not particularly limited and, for example, vacuum thermal dehydration method, dry heating method, γ ray irradiation method, UV irradiation method, electron beam irradiation method, X ray irradiation method, a method using a crosslinking agent and the like can be mentioned. Of these, a method using a crosslinking agent is preferable since, as mentioned below, even gelatin once formed like a sponge can be crosslinked with the same degree of crosslinking even to the inside of the sponge.

The crosslinking agent to be used is not particularly limited and, for example, glutaraldehyde, water-soluble carbodiimide such as EDC and the like, and condensing agent that produces a chemical bond between propylene oxide, diepoxy compound, hydroxyl group, carboxyl group, amino group, thiol group, imidazole group and the like (ethylene glycol diglycidyl ether, polyethylene glycol diglycidyl ether, polyglycerolpolyglycidyl ether, glycerolpolyglycidyl ether, hexamethylenediisocyanate etc.) can be used. Preferred is glutaraldehyde.

Crosslinking may be performed before freeze-drying or after freeze-drying. Specifically, for example, a sponge-like formed product is obtained by foaming an aqueous gelatin solution containing β-TCP by vigorously stirring the solution in a homogenizer and the like, performing a crosslinking reaction, casting the reaction mixture in a mold, and freezing and further freeze-drying the same, or foaming an aqueous gelatin solution containing β-TCP by vigorously stirring the solution in a homogenizer and the like, casting the reaction mixture in a mold, freezing and further freeze-drying to give a sponge-like formed product, and immersing the sponge-like formed product in a glutaraldehyde solution having a suitable concentration for a given time to perform crosslinking (see JP-A-2005-211477).

To discontinue a crosslinking reaction by glutaraldehyde, which is reactive with an amino group, for example, a low molecular substance having an amino group such as ethanolamine, glycine and the like only needs to be brought into contact therewith, or an aqueous solution having pH 2.5 or less may be added. To completely remove the crosslinking agent and low molecular substance used for the reaction, the obtained gelatin β-TCP sponge may be washed with distilled water, ethanol, 2-propanol, acetone and the like, and freeze-dried again.

A sponge structure critical as a scaffold material can be formed by foaming by stirring and freeze-dry step. That is, innumerable ice crystals grown by the freezing step become pores by freeze-drying, and a porous sponge structure having a desired pore ratio and a pore size can be formed.

Moreover, to avoid swelling of a sponge-like structure in the initial stage of a treatment with a crosslinking agent such as glutaraldehyde and the like, a thermal crosslinking treatment and the like may be applied before treatment. In addition, when crosslinking by a crosslinking agent is performed, toxicity is preferably removed by treating the reaction terminal. For example, after a glutaraldehyde treatment, toxicity can be removed by deactivating the reaction terminal by washing with aqueous glycine solution and the like.

The gelatin β-TCP sponge may be formed in any shape and can be formed in, for example, cylindrical form, prismatic form, sheet form, disc form, spherical form, particle and the like. The cylindrical, prismatic, sheet and disc forms are often generally used as embedded pieces, or can also be used as particles after pulverization. In addition, spherical form and particle form can also be administered in an injection.

As the gelatin β-TCP sponge, a commercially available product (e.g., enhanced β-TCP gelatin sponge MedGel (registered trade mark), Scaffold or MedGel (registered trade mark) SP (Medgel)) may be used.

3. Material for Induction of Hard Tissue Regeneration of the Present Invention

The "hard tissue" in the present invention means a tissue having a hard intercellular substance including bone, cartilage and teeth. The material for induction of hard tissue regeneration of the present invention is used as a material for induction of hard tissue regeneration since it contains PRP having a regeneration promoting effect on osteogenesis, chondrogenesis, angiogenesis and the like, and gelatin β-TCP sponge superior as a scaffold for tissue regeneration. Particularly, it is preferably used as a material for induction of regeneration of defective bone or cartilage tissue.

As mentioned above, while the material for induction of hard tissue regeneration of the present invention is preferably used as a material for induction of regeneration of defective bone or cartilage tissue requiring a cell scaffold, the applicable region thereof is not limited to a hard tissue, and may be a soft tissue in contact with a hard tissue such as bone or cartilage and the like. To be specific, the material induces regeneration of sinew and ligament by the angiogenesis promoting action of PRP even in the case of a transplant surgery of a soft tissue such as sinew, ligament etc. in contact with bone or cartilage. Therefore, such use for inducing regeneration of a soft tissue in contact with a hard tissue is also encompassed in the present invention.

The material for induction of hard tissue regeneration of the present invention can be widely used the fields of medicine and veterinary medicine including orthopedic and dental field, and the subject of application thereof is not limited to human, and includes mammals in general.

The material for induction of hard tissue regeneration of the present invention is prepared by adding PRP to the above-mentioned gelatin β-TCP sponge. PRP-containing gelatin β-TCP sponge can be obtained by, for example, adding dropwise PRP to the above-mentioned freeze-dried gelatin β-TCP sponge, or immersing gelatin β-TCP sponge in PRP to allow impregnation of the sponge with PRP. This immersing operation generally ends in 15 min-1 hr at 4-37° C., preferably 15-30 min at 4-25° C., during which the sponge is swollen with PRP, and a growth factor and the like contained in PRP interact with gelatin molecule in the sponge, whereby the growth factor and the like form a complex with the gelatin molecule, thus fixing PRP in the gelatin β-TCP sponge by a physical interaction. It is considered that not only the static interaction between them but also other interactions such as hydrophobic bond, hydrogen bond and the like greatly contribute to the formation of a complex between PRP and gelatin molecule.

The weight ratio of PRP to a gelatin β-TCP sponge (dry weight) is preferably within the range of about 1-fold to about 10000-fold. More preferably, PRP relative to a gelatin β-TCP sponge shows a weight ratio of about 2-fold to about 5000-fold, more preferably about 10-fold to about 1000-fold.

The material for induction of hard tissue regeneration of the present invention is directly embedded (applied to) in an affected part and can be devised to have an appropriate dosage form suitable for each use. That is, the gelatin β-TCP sponge may be formed to have a desired form such as cylindrical, prismatic, sheet, disc, spherical, particular form, and the like according to the application site thereof.

The dose of PRP in the material for induction of hard tissue regeneration of the present invention can be appropriately adjusted according to the severity of disease, and age, body weight and the like of the subject. In the case of a human, the dose for an adult patient is generally selected from the range of about 0.1-about 500 ml, preferably about 1-about 50 ml, and this can be administrated into an affected part or the vicinity thereof. When the effect obtained by a single administration is not sufficient, the administration can be performed multiple times.

The material for induction of hard tissue regeneration of the present invention may contain, where necessary, other appropriate medicaments and pharmacologically acceptable carriers. Examples of such medicament and carrier include a medicament that promotes angiogenesis and bone formation, an activator of osteoblast or an inhibitor of osteoclast, a scaffold carrier that promotes cell growth and differentiation, a combination thereof, and the like.

4. Effect of the Material for Induction of Hard Tissue Regeneration of the Present Invention 4.1 Effect of PRP Sustained Release Since the material for induction of hard tissue regeneration of the present invention shows both a PRP sustained-release effect and stabilization effect, a small amount thereof can exert the functions of various growth factors and the like contained in PRP for a long time. Consequently, the angiogenesis promoting function and osteogenesis, chondrogenesis ability of the growth factors and the like can be effectively exerted in the topically administered site.

The mechanism of sustained release is based on the fact that various growth factors and the like contained in PRP are physically fixed on gelatin β-TCP in the sponge. The present inventors have heretofore tried sustained release of growth factor, cytokine, monokine, lymphokine, other physiologically active substances and the like by using a bioabsorbable polymer hydrogel, and succeeded in a sustained release of a growth factor and the like having a physiological activity unachievable by other materials, and control of the duration of the sustained release. In the present invention, the growth factor and the like contained in PRP are considered to be released in a sustained manner from gelatin β-TCP due to a similar mechanism. A growth factor etc. fixed on gelatin β-TCP are not released from the sponge. Along with the degradation of gelatin β-TCP sponge in the body, gelatin β-TCP molecule becomes water soluble, which causes release of the growth factor and the like fixed on the gelatin β-TCP molecule. That is, degradation of gelatin β-TCP sponge enables control of sustained release of the growth factor and the like. The degradability of gelatin β-TCP sponge can be altered by controlling the degree of crosslinking during production of the gelatin β-TCP sponge. In addition, since various growth factors and the like contained in PRP interact with gelatin β-TCP, their stability in the body, for example, resistance to enzymatic degradation and the like, is improved. Moreover, since gelatin β-TCP sponge disappears along with the sustained release of growth factor and the like, the bone formation process due to the growth and differentiation of cells is not physically inhibited.

4.2 Angiogenesis-Promoting and Osteogenesis and Chondrogenesis Promoting Effect

The PRP to be contained in the material for induction of hard tissue regeneration of the present invention contains various growth factors and the like, and provides various effects such as angiogenesis promoting effect, osteogenesis promoting effect, chondrogenesis promoting effect, wound healing promoting effect, skin ulcer treatment effect and the like (as mentioned above).

As shown in the below-mentioned Examples, the inventors have confirmed that the material for induction of hard tissue regeneration of the present invention has a remarkable bone forming action. Ossification is reported to involve angiogenesis and, combined with the contribution of osteogenesis and chondrogenesis promoting effect but also various effects of PRP such as angiogenesis promoting effect etc., tissue regeneration is promoted in the defective region and good bone formation is achieved.

4.3 Effect as Scaffold Material

The material for induction of hard tissue regeneration of the present invention comprises a crosslinked gelatin β-TCP sponge as a main component, and a substrate having many ultrafine pores having a given pore size. Thus, the material permits easy entry of cells and can function as a scaffold material for regeneration. In addition, since PRP component is electrostatically bound to the surface of the substrate and released in a sustained manner along with the decomposition of the substrate, it can act on the cell for a long time, thus strikingly increasing the ossification effect. The rate of sustained release can be controlled by adjusting the degree of crosslinking of gelatin. That is, the material for induction of hard tissue regeneration of the present invention can simultaneously play two roles of a scaffold material for regeneration and a regeneration promoter.

EXAMPLES

The present invention is explained in more detail in the following by referring to Examples, which are not to be construed as limitative.

Examples

1. Preparation of Platelet-Rich Plasma (PRP)

SD rat (male, 8-week-old, 240-290 g, SHIMIZU Laboratory Supplies Co., Ltd., Kyoto) was placed under general anesthesia by intraperitoneal injection of pentobarbital (250 µL). The chest was opened and blood (5 CC) was drawn from the heart using a 21 G needle. The blood was transferred to a 15 cc centrifugal tube containing ACD-A solution (W/V %: citric acid 0.85, trisodium citrate 2.32, glucose 2.59) (2 CC) in advance. The centrifugal tube was centrifuged in a centrifuge (KN-70, manufactured by KUBOTA CORPORATION) at 1500 rpm for 10 min. After centrifugation, a transparent serum portion in the upper layer was suctioned with a 14 G Surflo needle and transferred to another centrifugal tube and centrifuged at 3000 rpm for 10 min. The serum portion in the upper layer was suctioned with a 14 G Surflo needle leaving 200 and the remaining solution was stirred to give platelet-rich plasma (PRP) (200 µL). A gelatin β-TCP sponge cut into a 2 mm cube (β-TCP-reinforced gelatin sponge MedGel (registered trade mark) Scaffold (MedGEL CO., LTD.), total 20 mg) was immersed in the obtained PRP (200 µL) and left standing at 4° C. overnight. As a control, a gelatin β-TCP sponge in the same amount and shape was immersed in phosphate buffer saline (hereinafter PBS, 200 µL) and left standing at 4° C. overnight.

2. Rat Spinal Posterolateral Fusion Model

SD rat (male, 8-week-old, 240-290 g, SHIMIZU Laboratory Supplies Co., Ltd., Kyoto) was placed under general anesthesia by intraperitoneal injection of pentobarbital (250 µL). The skin in the median back was longitudinally incised for 40 mm. The paraspinal muscle was longitudinally incised for 25 mm at 5 mm right and left from the midline, and the transverse processes of the fourth and fifth lumbar vertebrae (hereinafter transverse processes 4, 5) were exposed on the both sides. Using a steel bar with a 0.5 mm diameter tip (OSADASUCCESS-40M, OS-40MV, manufactured by OSADA, INC.), the dorsal cortical bone of the transverse processes was drilled until confirmation of the bleeding from the bone marrow. The materials shown below were transplanted in between the transverse processes 4, 5, and the incised paraspinal muscles and skin were sutured with a 3-0 nylon thread (manufactured by company). The materials to be transplanted were 1: PRP impregnated gelatin β-TCP sponge (hereinafter PRP sponge), 2: PBS (phosphate buffer saline) impregnated gelatin β-TCP sponge (MedGel (registered trade mark) Scaffold (MedGEL CO., LTD.): hereinafter, PBS sponge), 3: PRP alone, 4: autologous iliac bone, and no-transplantation group, total 5 groups. In the PRP alone model of 3, only 200 µL of PRP was sprayed in between the transverse processes. As the self-ilium of 4, the tip of ilium on the same side as the scheduled transplantation site was taken in the size of in 5×2×2 mm. FIG. 1 schematically shows transplantation in between transverse processes 4, 5 in rat spinal posterolateral fusion model.

3. Evaluation of Ossification and Evaluation of Mechanical Strength

At 8 weeks after the operation, the rat was euthanized by high dose administration of pentobarbital, and the lumbar vertebrae were isolated. Using µCT (microfocus 2D/3D X-ray CT apparatus, ScanXmate-E090S40, manufactured by Comscantecno Co., Ltd.), sagittal reconstitution images of the transverse processes 4, 5 were formed, and the presence or absence of concrescence between the transverse processes was evaluated. In addition, based on the obtained images and using an image analysis software (FanCT ver1.3 manufactured by Comscantecno Co., Ltd.), only the part between the transverse processes was extracted and the bone mass was measured. Thereafter, a three-point bending test of the lumbar vertebrae was carried out by a three-point bending test machine (TOKYO TESTING MACHINE, LSC-200/30-2). The lumbar vertebrae were set with the front facing upward on a fixture with a span of 40 mm, and the 4/5 lumbar disc front was pressed at speed of 10 mm/min using a cylindrical fixture (diameter 5 mm). The load at the time point when the displaced distance was 10 mm was compared between groups. Then, the tissue was fixed with 4% para-formaldehyde at 4° C. for 1 week. The tissue was decalcified with 0.5M EDTA (ethylenediaminetetraacetic acid) solution for 2 weeks and immersed in 20% sucrose for 2 days. A frozen tissue section (thickness 12 μm) between transverse processes 4, 5 was prepared and stained with hematoxylin-eosin and safranine O (cartilage substrate was stained red).

4. Results

Figure 2:
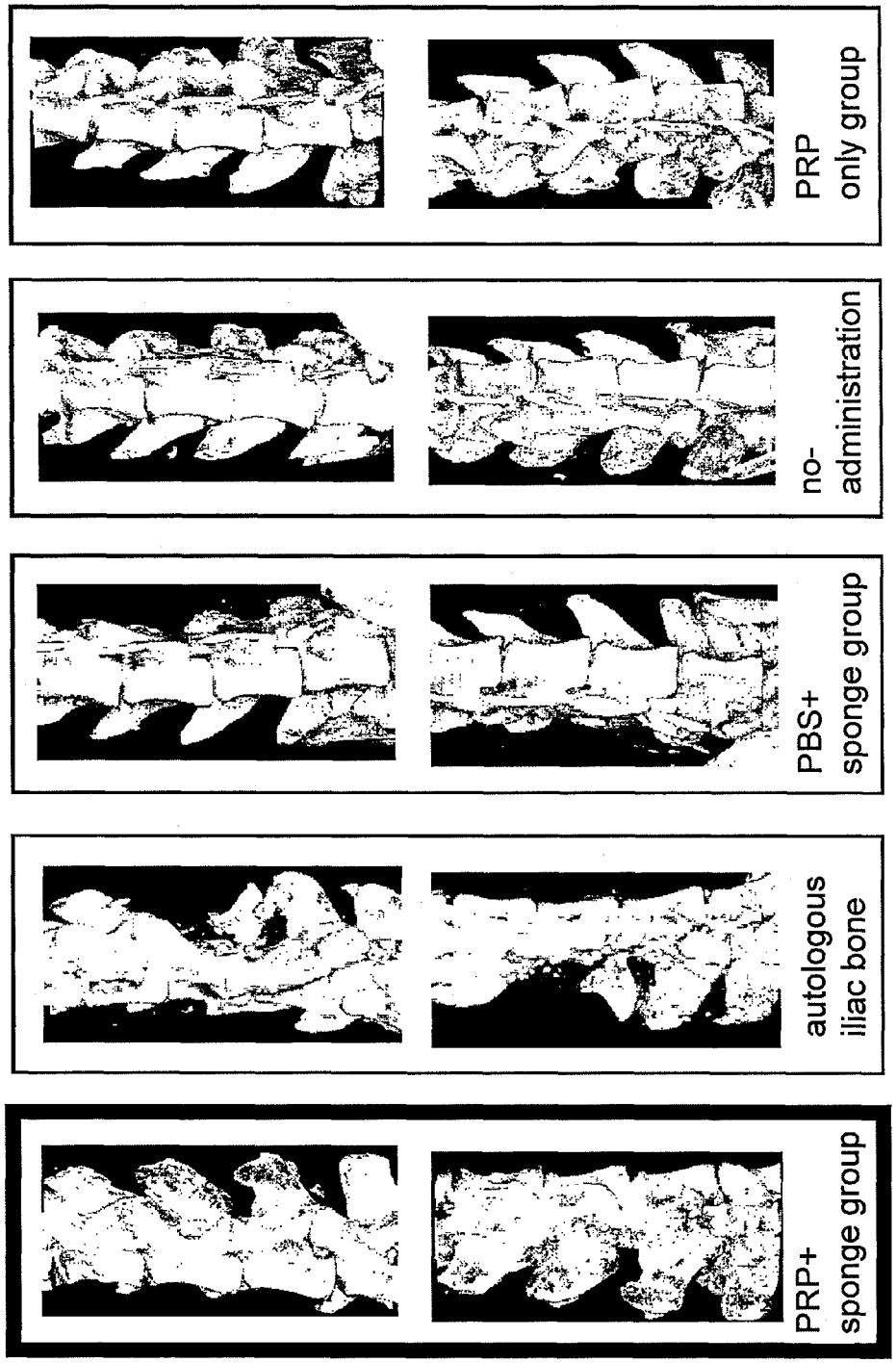
FIG. 2 shows sagittal section reconstitution images of left and right transverse processes 4, 5.

FIG. 2 shows the results of the sagittal section reconstitution images of the left and right transverse processes 4, 5. The PRP sponge model and autologous iliac bone model were found to show concrescence tendency between the left and right transverse processes. In addition, the PRP sponge model showed marked increase of anteroposterior diameter of transverse processes, as compared to the autologous iliac bone model. The PBS sponge, single PRP and no-transplantation model did not show an increase between transverse processes and a synostosis tendency was not found.

Figure 3:
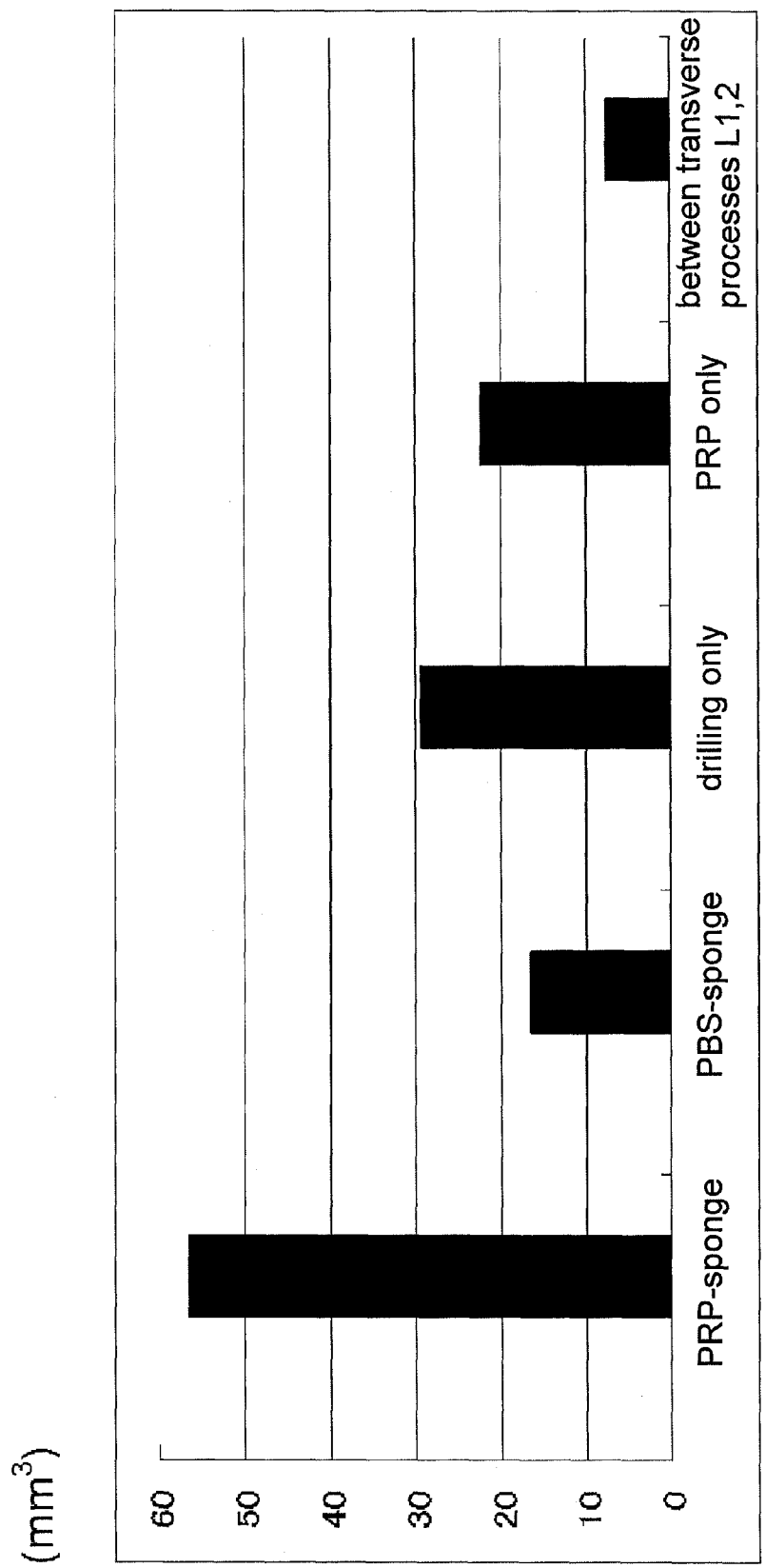
FIG. 3 is a graph showing the bone mass between transverse processes.

FIG. 3 shows the bone mass between transverse processes 4, 5. The PRP sponge model showed a remarkable increase of the bone mass as compared to the other models.

Figure 4:
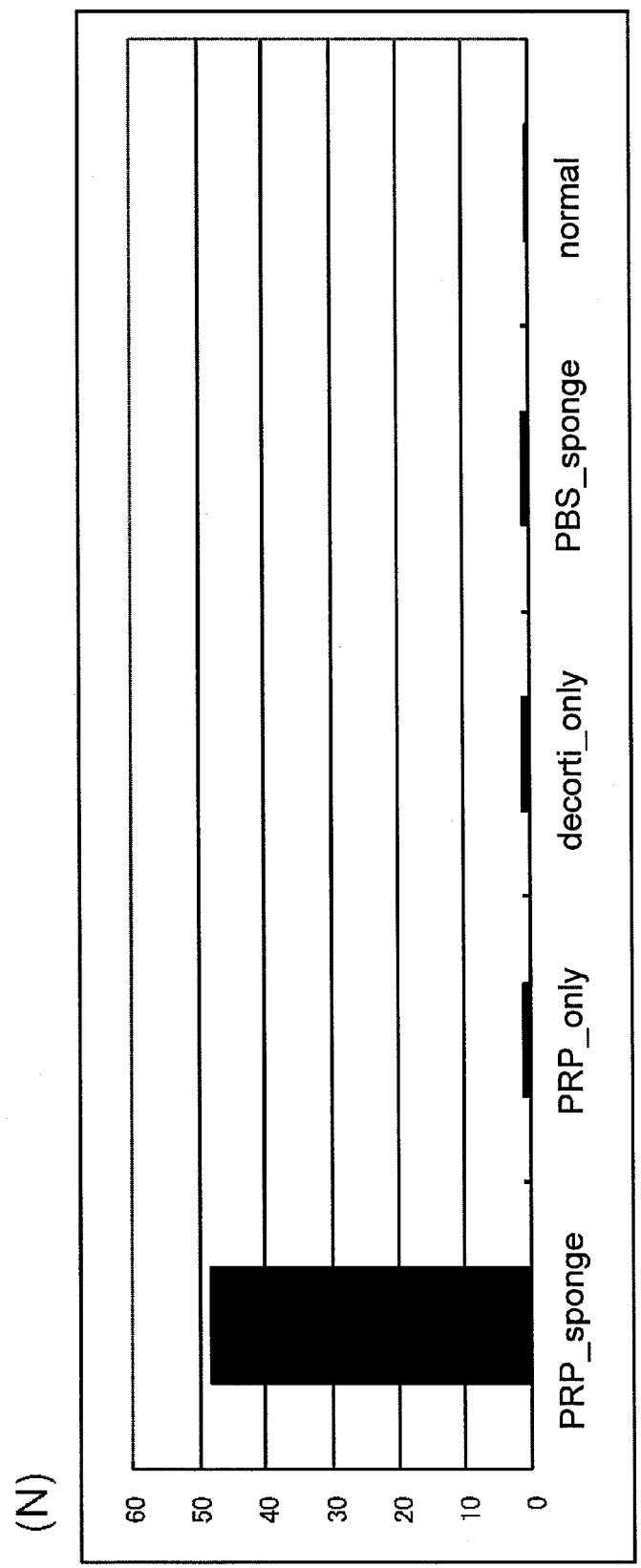
FIG. 4 is a graph showing the results of a 3-point bending test.

FIG. 4 shows the results of the three-point bending test. The PRP sponge model showed 59.6-fold strength on average as compared to the other groups.

Figure 5:
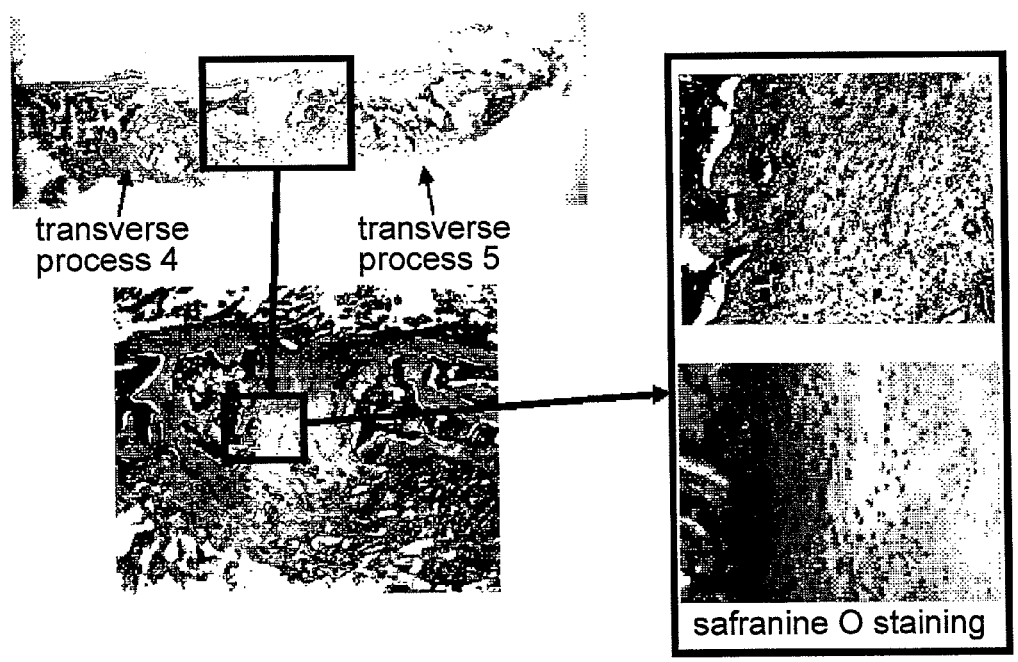
FIG. 5 shows tissue images between transverse processes 4, 5 of a PRP sponge model. Ossification-like changes are observed in the cartilage between transverse processes. In [comparison], no-transplantation group (8 weeks post-operation), a ligament component is observed between transverse processes, but bone and cartilage components are not observed, wherein arrows always show left: transverse process 4, right: transverse process 5, and upper right images show safranine O-stained images.
Figure 5:
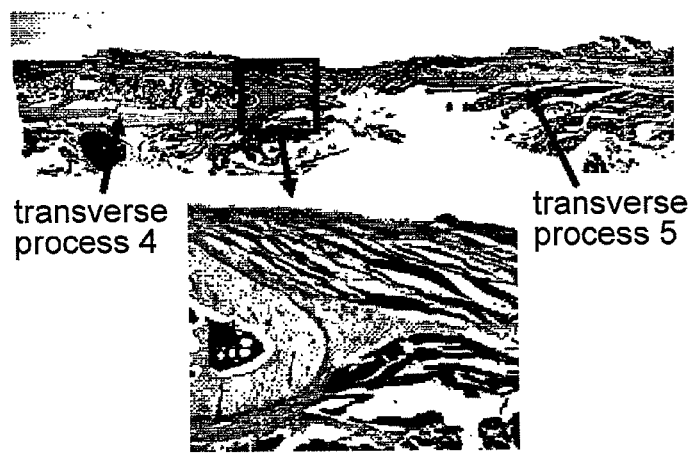

FIG. 5 shows tissue images between transverse processes 4, 5 of PRP sponge model. Between transverse processes, bone substrate and hyaline cartilage components are mixed in the images, and an intracartilaginous ossification-like phenomenon was observed. By safranine O-staining, a part around hyaline cartilage showed a red stained image, verifying it is a cartilage substrate. For comparison, tissue images (8 weeks post-operation) between transverse processes 4, 5 of no-transplantation group is shown. As shown in FIG. 5, ligament component is observed between transverse processes, but bone and cartilage components are not observed.

5. Conclusion

From the above results, it has been verified that a combination of PRP and gelatin β-TCP sponge achieves an extremely high bone or cartilage formation ability exceeding that of autogenous bone transplantation, and the mechanical strength at the synostosis part is markedly potentiated.

Reference Example

Production of Gelatin β-TCP Sponge

As gelatin, an acid-treated product manufactured by Nitta Gelatin Inc. (acid-treated gelatin) was used. As β-TCP, β-TCP-100 (pulverized product, Taihei Chemical Industrial Co., Ltd.) was used. OSferion may also be used.

The acid-treated gelatin was dissolved in distilled water to give 3 wt % aqueous gelatin solution. To the obtained aqueous gelatin solution (60 mL) was added β-TCP (1.8 g) and 0.16 wt % aqueous glutaraldehyde solution (0.4 mL) was added, and the mixture was stirred in a homogenizer at 5000 rpm for 3 min to allow foaming. The foamed aqueous gelatin β-TCP solution was cast in a 12 cm×12 cm mold, left standing at 4° C. for 12 hr to perform a crosslinking reaction, after which the solution was frozen at −40° C. and freeze-dried to give a sponge.

The obtained sponge was washed 3 times with 0.1N aqueous glycine solution for 1 hr, further washed with water, and freeze-dried again to give a gelatin β-TCP sponge.

All publications, patents and patent applications cited in the specification are hereby incorporated in their entireties by reference.

INDUSTRIAL APPLICABILITY

Platelet-rich plasma used in the present invention does not require special facilities and equipment, since it can be purified by centrifugation of the own blood of the subject to be applied with a material for induction of hard tissue regeneration. Therefore, the present invention can be practiced in many facilities. In addition, since platelet-rich plasma derived from own blood is used, the possibility of side effects is extremely low as compared to gene recombinant growth factor. Furthermore, since gelatin β-TCP sponge comprises only the materials in clinical use and has high safety for the human body, the material for induction of hard tissue regeneration of the present invention is expected to be extremely rapidly subjected to clinical application. The diffusion of the present invention dramatically decreases the need for collection of autogenous bone, which has been generally performed conventionally, and the ossification promoting action enables early loading and early rehabilitation. Hence, the benefit thereof is immeasurable.

The invention claimed is:

1. A material for induction of hard tissue regeneration, comprising platelet-rich plasma and a gelatin β-TCP sponge, wherein the gelatin constituting the gelatin β-TCP sponge is an acidic gelatin.

2. The material according to claim 1, wherein the hard tissue is a bone or a cartilage tissue.

3. The material according to claim 1, which promotes osteogenesis or chondrogenesis.

4. The material according to claim 1, which promotes angiogenesis.

5. The material according to claim 1, wherein the platelet-rich plasma is derived from a subject to be applied with a material for induction of hard tissue regeneration.

6. The material according to claim 1, wherein the gelatin β-TCP sponge has a pore size of 10-500 μm.

7. The material according to claim 1, wherein the gelatin in the gelatin β-TCP sponge is crosslinked.

8. The material according to claim 1, wherein the gelatin β-TCP sponge is prepared by crosslinking and freeze-drying a composition comprising β-TCP and gelatin.

9. The material according to claim 1, wherein the gelatin β-TCP sponge is crosslinked and has a pore size of 10-500 μm.

* * * * *